US010955657B2

(12) United States Patent
Shameli et al.

(10) Patent No.: US 10,955,657 B2
(45) Date of Patent: Mar. 23, 2021

(54) ENDOSCOPE WITH DUAL IMAGE SENSORS

(71) Applicants: Acclarent, Inc., Irvine, CA (US); Biosense Webster (Israel) Ltd., Yokneam (IL)

(72) Inventors: Ehsan Shameli, Irvine, CA (US); Yehuda Algawi, Binyamina (IL); Assaf Govari, Haifa (IL); Babak Ebrahimi, Irvine, CA (US); Fatemeh Akbarian, Rancho Palos Verdes, CA (US); Jetmir Palushi, Irvine, CA (US); Moran Levi, Kiryat-Tivon (IL); Noam Racheli, Hadera (IL)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/695,500

(22) Filed: Nov. 26, 2019

(65) Prior Publication Data
US 2020/0201022 A1 Jun. 25, 2020

Related U.S. Application Data

(60) Provisional application No. 62/782,697, filed on Dec. 20, 2018.

(51) Int. Cl.
*G02B 23/24* (2006.01)
*A61B 1/00* (2006.01)

(52) U.S. Cl.
CPC ........ *G02B 23/2415* (2013.01); *A61B 1/0005* (2013.01); *A61B 1/00096* (2013.01); *A61B 1/00193* (2013.01); *G02B 23/243* (2013.01)

(58) Field of Classification Search
CPC ............................ A61B 34/20; G02B 23/2415
See application file for complete search history.

(56) References Cited

U.S. PATENT DOCUMENTS 7,720,521 B2 * 5/2010 Chang .................... A61B 17/24
600/424
9,198,835 B2 * 12/2015 Swisher ............. A61B 1/00144
(Continued)

FOREIGN PATENT DOCUMENTS

JP          H09-5643 A      1/1997
WO    WO 2009/144729 A1   12/2009

OTHER PUBLICATIONS

International Search Report and Written Opinion dated Mar. 18, 2020 for International Application No. PCT/IB2019/060797, 15 pages.

(Continued)

*Primary Examiner* — Paulos M Natnael
(74) *Attorney, Agent, or Firm* — Frost Brown Todd LLC

(57) ABSTRACT

An endoscopic camera has two or more cameras positioned at a distal end, positioned to provide partially overlapping fields of view. The cameras communicate captured digital images the length of the flexible endoscope, where they may be saved and processed to provide additional imaging features. With partially overlapping images from two or more cameras, image processing can provide panoramic images, super resolution images, and three-dimensional images. One or more of these image modes may also be enhanced to provide a virtualization window that displays a portion of a larger or higher resolution image. The virtualization window displays the selected area of the image, and may be moved or zoomed around the image to provide a virtual endoscope repositioning experience, where the endoscope remains statically positioned but the virtualization window presents a sense of movement and navigation around the surgical area.

20 Claims, 10 Drawing Sheets

(56) References Cited

U.S. PATENT DOCUMENTS

| | | | | |
|---|---|---|---|---|
| 9,585,813 | B2* | 3/2017 | Dorsey | A61B 1/0005 |
| 10,314,559 | B2* | 6/2019 | Razzaque | A61B 34/25 |
| 10,516,865 | B2* | 12/2019 | Sidar | G06T 5/009 |
| 2010/0331883 | A1* | 12/2010 | Schmitz | A61B 17/1604 |
| | | | | 606/249 |
| 2014/0210945 | A1 | 7/2014 | Morizumi et al. | |
| 2014/0364725 | A1* | 12/2014 | Makower | A61M 25/09 |
| | | | | 600/424 |
| 2015/0018618 | A1 | 1/2015 | Ikeda | |
| 2015/0018622 | A1* | 1/2015 | Tesar | A61B 50/13 |
| | | | | 600/202 |
| 2015/0238073 | A1* | 8/2015 | Charles | A61B 90/20 |
| | | | | 600/102 |
| 2016/0008083 | A1 | 1/2016 | Kesten et al. | |
| 2016/0335751 | A1* | 11/2016 | Sidar | H04N 9/646 |
| 2018/0368656 | A1* | 12/2018 | Austin | A61B 1/00039 |
| 2019/0206565 | A1* | 7/2019 | Shelton, IV | A61B 34/74 |
| 2020/0107886 | A1* | 4/2020 | Govari | A61B 5/066 |
| 2020/0184640 | A1* | 6/2020 | Mahadik | G06T 7/0012 |
| 2020/0196851 | A1* | 6/2020 | Shameli | A61B 1/00158 |
| 2020/0201022 | A1* | 6/2020 | Shameli | G02B 23/2484 |

OTHER PUBLICATIONS

U.S. Appl. No. 62/779,614, entitled "Surgical System with Combination of Sensor-Based Navigation and Endoscopy," filed Dec. 14, 2018.

* cited by examiner

| INSTRUMET PANEL 58 | CAMERAS 59 | SHAFT 52 | COUPLING UNIT 54 |
| --- | --- | --- | --- |
| IRRIGATION CHANNEL 62 | LIGHT 64 | | CONTROL 56 |

ENDOSCOPE WITH DUAL IMAGE SENSORS

PRIORITY

This application claims priority to U.S. Provisional Patent 62/782,697, filed Dec. 20, 2018 and entitled Endoscope with Dual Image Sensors, the disclosure of which is incorporated by reference herein.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MRI, 3D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

While IGS navigation systems provide useful views and information during a surgical procedure, a surgeon may also desire real-time photographs and video of an anatomical structure being operated on. In such cases, an endoscope may be deployed to the surgical site with the aid of IGS navigation in order to capture images of the anatomical structure, and may also be paired with or otherwise deployed with other surgical instruments, such as cutting tools. Photographic images and video captured in this manner may be more useful than IGS navigation images, which may only provide generalized and simulated images.

Images captured by an endoscope may also be somewhat limited as compared to direct visual observation by a surgeon, as they are limited to two dimensional (2D) representations of an anatomical structure. As a result, cutting, cauterizing, and other critical actions may be performed using a combination of 2D endoscopy and IGS navigation, neither of which can provide the sense of depth perception available with true three dimensional (3D) observation. Manipulating and operating surgical tools without the benefit of 3D observation can increase the time spent positioning tools, and can increase the possibility of error. While some 3D endoscopic cameras exist, they have a high complexity and cost, and are most commonly available in variations having rigid and inflexible portions, making them difficult or impossible to use for some procedures. Implementations having both flexibility and 3D features require expensive and fragile fiber optic components to transfer captured images, as light, from a distal camera to a proximal viewer. As a result, conventional options for 3D endoscopy are expensive, limited in available features, and unsuitable for high volume use and disposability.

While several systems and methods have been made and used in surgical procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figures 1, 2:
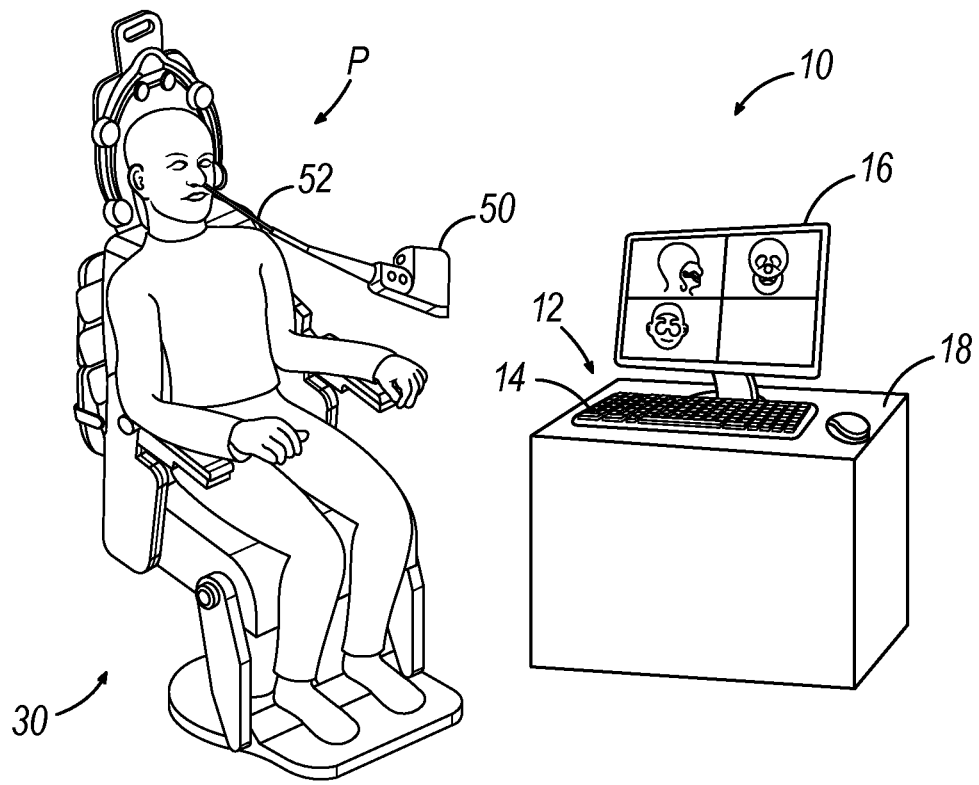
FIG. 1 depicts a schematic view of an exemplary surgery navigation system being used on a patient seated in an exemplary medical procedure chair.
FIG. 2 depicts a schematic view of an exemplary dual camera endoscope.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

I. EXEMPLARY IMAGE GUIDED SURGERY NAVIGATION SYSTEM

When performing a medical procedure within a head of a patient (P), it may be desirable to have information regarding the position of an instrument within the head of the patient (P), including endoscopic images. FIG. 1 shows an exemplary IGS navigation system (10) enabling an ENT procedure to be performed using image guidance. In addition to or in lieu of having the components and operability described herein IGS navigation system (10) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

A processor (12) of IGS navigation system (10) comprises one or more processing units (e.g., a microprocessor, logic processor, or other circuitry usable to execute programming instructions) communicating with one or more memories. The processing units and memories may be positioned proximately to the IGS navigation system (10) (e.g., may be within a computer or other equipment in a surgical suite where the IGS navigation system (10) is in use) or may be positioned in remote locations and in communication with the IGS navigation system (10) over a network (e.g., may be within a computer, server, or other equipment outside of the surgical suite, such as elsewhere in a hospital, at a different building, or in a cloud hosted environment).

Processor (12) of the present example is mounted in a console (18), which comprises operating controls (14) that include a keypad and/or a pointing device such as a mouse or trackball. A physician uses operating controls (14) to interact with processor (12) while performing the surgical procedure. Processor (12) uses software stored in a memory of processor (12) to calibrate and operate IGS navigation system (10). Such operation includes processing data from instruments such as a dual camera endoscope (50), which includes a shaft (52) that is flexible and insertable into the patient's head to capture video and images within. In some versions, the distal portion of endoscope (50) includes one or more position sensors that are operable to generate signals indicating the position of the distal portion of endoscope (50) within the head of the patient (P). Such position sensing capabilities may be provided in accordance with the teachings of various references cited herein.

Operations by processor (12) may also include processing data from operating controls (14) and driving display screen (16). Processor (12) is further operable to provide video in real time via display screen (16) which may include showing an endoscopic image (e.g., captured via the dual camera endoscope (50)), a pre-operative CT scan image of the patient's head, and/or a computer generated three-dimensional model of the anatomy within and adjacent to the patient's nasal cavity. Display screen (16) may display such images simultaneously and/or superimposed on each other during the surgical procedure. By way of example only, display screen (16) may provide images in accordance with at least some of the teachings of U.S. Pub. No. 2016/0008083, entitled "Guidewire Navigation for Sinuplasty," published Jan. 14, 2016, issued as U.S. Pat No. 10,463,242 on Nov. 5, 2019, the disclosure of which is incorporated by reference herein.

The images provided through display screen (16) may help guide the operator in maneuvering and otherwise manipulating instruments within the patient's head. Some implementations of the IGS navigation system (10) may also provide various other IGS navigation features, including real-time positional tracking of surgical instruments, overlaying of tracked positions on pre-operative images, and using tracked positions of surgical instruments to provide information, guidance, and safety alerts during a procedure, as will be apparent to one of ordinary skill in the art in light of the teachings herein.

II. EXEMPLARY DUAL SENSOR ENDOSCOPE

Use of the dual camera endoscope (50) to display images via a display such as the display screen (16) may be advantageous in preparation for, during, and after surgical procedures. By including multiple (e.g., two, in the case of the dual camera endoscope (50), but other implementations may include three or more) cameras or other types of image sensors, additional image data can be captured and used to provide a number of advantageous features such as improved resolution, improved field of view, three-dimensional image depth, and others, as will be described in more detail below.

FIG. 2 shows a schematic view of an endoscope such as the exemplary dual camera endoscope (50). The dual camera endoscope (50) includes a coupling unit (54) and control (56) at a proximal end of the device, a shaft (52) that flexibly extends from the proximal end of the device. A set of cameras (59) is positioned at a distal end of the shaft (52) and are operable to capture images within their field of view. In some implementations, the set of cameras (59) may include one or more image sensors or image capture devices positioned at the distal end of the shaft (52) that are connected to a device such as the coupling unit (54) via one or more cables, wires, or other connections extending along the length of shaft (52) that are capable of carrying digital image data from the image sensors to the coupling unit (54). In some implementations, the set of cameras (59) may include one or more image or sensors or image capture devices positioned at a proximal end of the shaft (52), with corresponding optical transmitters, such as optical fibers, extending along the length of the shaft (52). In such an implementation, each corresponding optical fiber may be coupled with a lens at the distal end to capture and focus light (e.g., images) into the optical fiber to be transported to the proximally positioned image capture devices or image sensors.

Also positioned at the distal end of the shaft (52) are a light (64) (e.g., an LED, optical fiber, infrared light source, or other lighting element) operable to provide illumination or transillumination of a surgical site. In some implementations, the set of cameras (59) and the light (64) may be selected to complement each other, such as a camera capable of high frame rate image capture being paired with a bright light, a camera with infrared sensors being paired with an infrared light, or a camera capable of low-light image capture being paired with a dim or moderately bright light. The distal end of the shaft (52) also includes one or more irrigation channels (62) that may be used to provide fluid at a surgical site, wash the covers or lenses of the set of cameras (59) and the light (64), or remove fluid from a surgical site (e.g., by providing suction), for example. Also included is an instrument channel (58), through which other flexible instruments may be advanced from the proximal end of the shaft (52) to a distal end, to aid in navigation of such instruments to a surgical site. As noted above, the dual camera endoscope (50) may also include a position sensor (not shown) that may be tracked by one or more instrument tracking features of the IGS navigation system (10), where such features are provided.

The control (56) may be interacted with by a user to configure, enable, or disable one or more features of the dual camera endoscope (50), such as turning the set of cameras (59) or the light (64) on, or causing the irrigation channel (62) to provide fluid for cleaning. The coupling unit (54) may provide communication with one or more other devices of the IGS navigation system (10), such as the processor (12). The coupling unit (54) may be communicatively connected with the processor (12) via a wired (e.g., USB, optical fiber, ethernet) or wireless (e.g., Wi-Fi, Bluetooth) connection, and may be configured to provide image data captured by the set of cameras (59) to the processor (12) so that captured images may be displayed via the display screen (16).

Figure 3A:
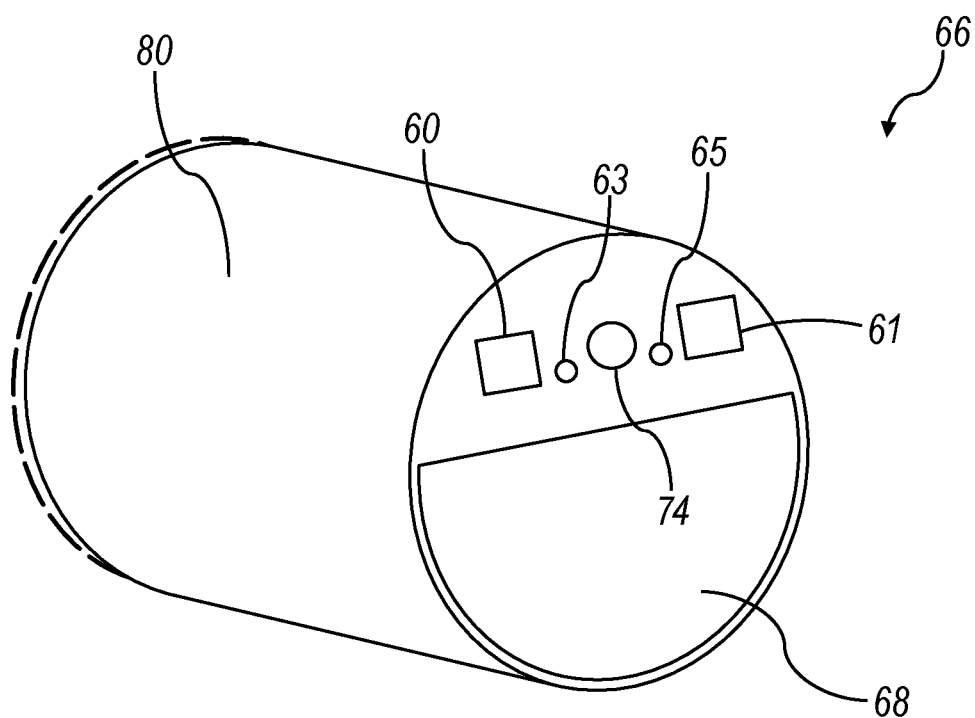
FIG. 3A depicts a front perspective view of a distal tip of the dual camera endoscope of FIG. 2.
Figure 3B:
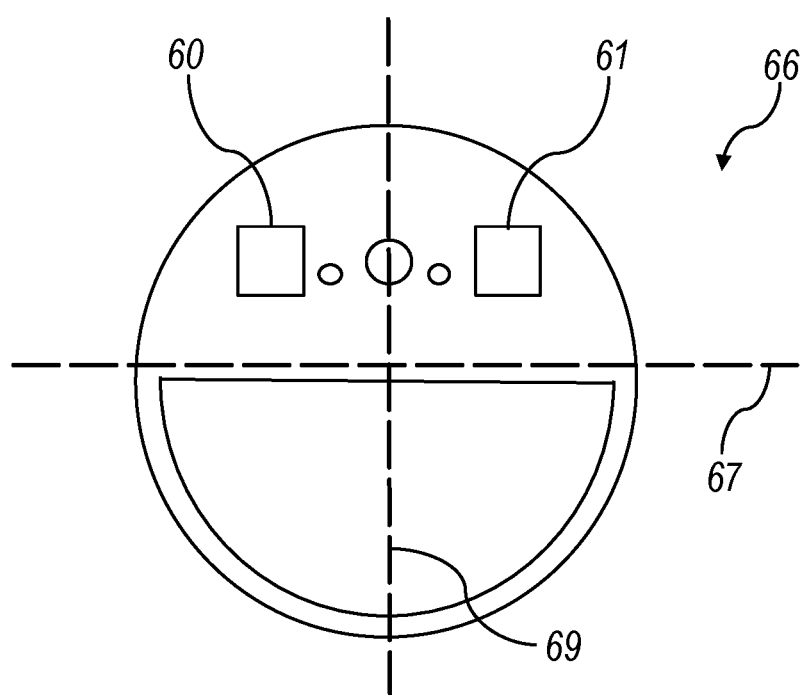
FIG. 3B depicts a simulated coordinate system overlaid on a front elevation view of the distal tip of FIG. 3A.

FIG. 3A shows a front perspective view of a distal tip of an endoscope such as the dual camera endoscope (50). A distal portion of a shaft (80), having similar features and function as the shaft (52), includes a distal tip (66). The distal tip (66) includes a light (74), having similar features and function as the light (64), and an instrument channel (68), having similar features and function as the instrument channel (58). The distal tip (66) also includes a first camera (60) and a second camera (61), having similar features and functions as the set of cameras (59). As can be seen with reference to FIG. 3B, which depicts a coordinate system overlaid upon a front elevation view of the distal tip (66), the first camera (60) and the second camera (61) are located at different coordinates of a horizontal axis (67), while being at substantially the same coordinate on a vertical axis (69). In this manner, images captured by the first camera (60) and the second camera (61) may be of two different field of views that are offset from each other along the first axis, while substantially matching along the second axis. The first camera (60) and the second camera (61) may be the same type of camera, and may have similar capabilities in terms of speed, quality, and visual characteristics for image capture.

It may be advantageous to implement the first camera (60) and the second camera (61) as digital imaging devices capable of capturing image data digitally at the distal tip (66), and providing the image data as electronic signals to the coupling unit (54) via a set of flexible data connections (not shown) within the shaft (52). The flexible data connections (not shown) may flex as the shaft (52) flexes, without providing significant resistance or being severed by the result of such flexing. Additionally, the set of flexible data connections (not shown) may be made of materials and configurations (e.g., copper or aluminum data cabling, solid or stranded data cabling) less expensive and less fragile than fiber optic cables, and so may be advantageous for transmitting images and image data from the distal tip (66) to the coupling unit (54) via the shaft (52) in such implementations. With the set of cameras (59) positioned as they are in FIG. 3A, the light (64) may be advantageously positioned substantially equidistantly between in order to provide similar lighting to each of the first camera (60) and the second camera (61) during use, such that output images captured simultaneously by each camera will have substantially similar lighting and other visual characteristics.

The distal tip (66) shown in FIG. 3A also includes an outlet for a first channel (63) and a second channel (65), having similar features and function as the irrigation channels (62), and each positioned proximately to a corresponding camera of the set of cameras (59). In this manner, the first channel (63) may be operated to provide cleaning and irrigation fluid directed at a cover or lens of the first camera (60), while the second channel (65) may be operated to provide cleaning and irrigation fluid directed at a cover or lens of the second camera (61). Separate channels of the irrigation channels (62), such as the first channel (63) may be operated in different modes (e.g., by using a set of valves to direct fluid to a particular nozzle, or by varying pressure of fluid provided to open one or more pressure release valves) to provide general irrigation at the site, provide irrigation directed at a corresponding camera, or both, as may be desired for a particular implementation. For example, in one implementation fluid provided at a first, lower pressure may direct a stream of fluid from a first nozzle of the first channel (63) at the first camera (60). Providing the fluid at a second, higher pressure may cause a release valve at a distal end of the first channel (63) to open and provide fluid from a second nozzle of the first channel (63) to provide general irrigation of the area.

Figure 4A:
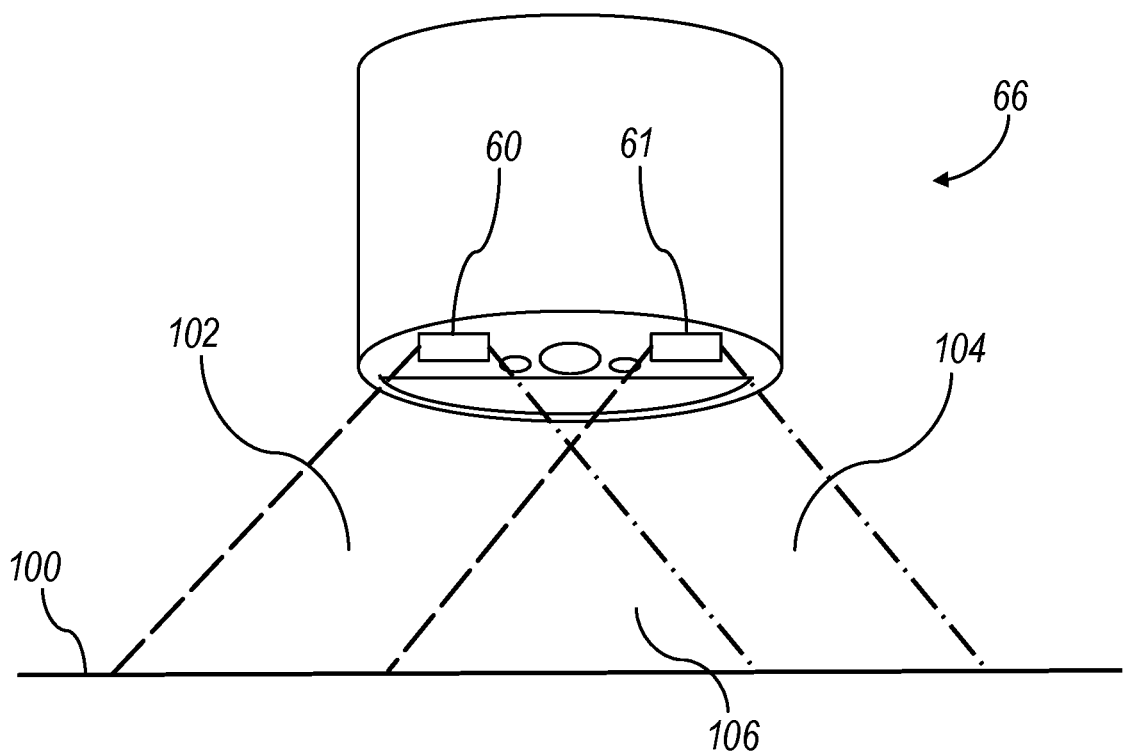
FIG. 4A depicts a side diagrammatic view of an exemplary set of partially overlapping fields of view of the dual camera endoscope of FIG. 2.
Figure 4B:
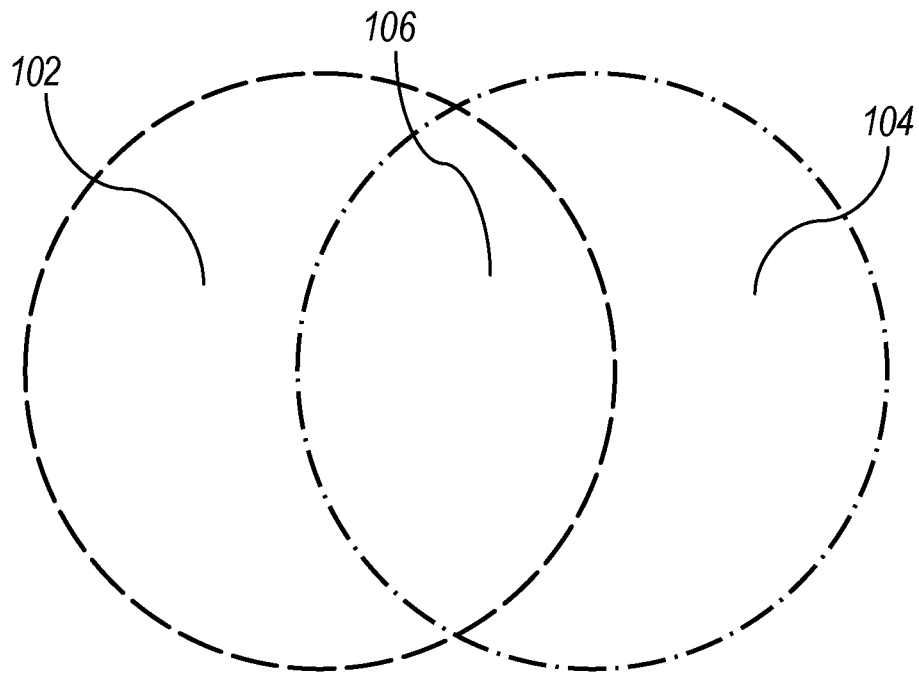
FIG. 4B depicts a top-down diagrammatic view of the set of partially overlapping fields of view of FIG. 4A.

One advantage of positioning the set of cameras (59) as seen in FIG. 3A is to provide image data from two separate fields of view, which may partially or fully overlap in varying implementations. For example, FIG. 4A depicts a side diagrammatic view of an exemplary set of partially overlapping fields of view that may be captured using an endoscope such as the dual camera endoscope (50), while FIG. 4B depicts a top-down diagrammatic view of the set of partially overlapping fields of view. As can be seen, the first camera (60) and the second camera (61) are oriented such that their respective lines of sight to a target surface (100) are parallel. The first camera (60) provides a first field of view (102) of the target surface (100), while the second camera (61) provides a second field of view (104) of the target surface (100). The first field of view (102) and the second field of view (104) also combine to provide a combined field of view (106), in which the target surface (100) is viewed by each camera, in parallel, from a slightly different position.

Figure 5A:
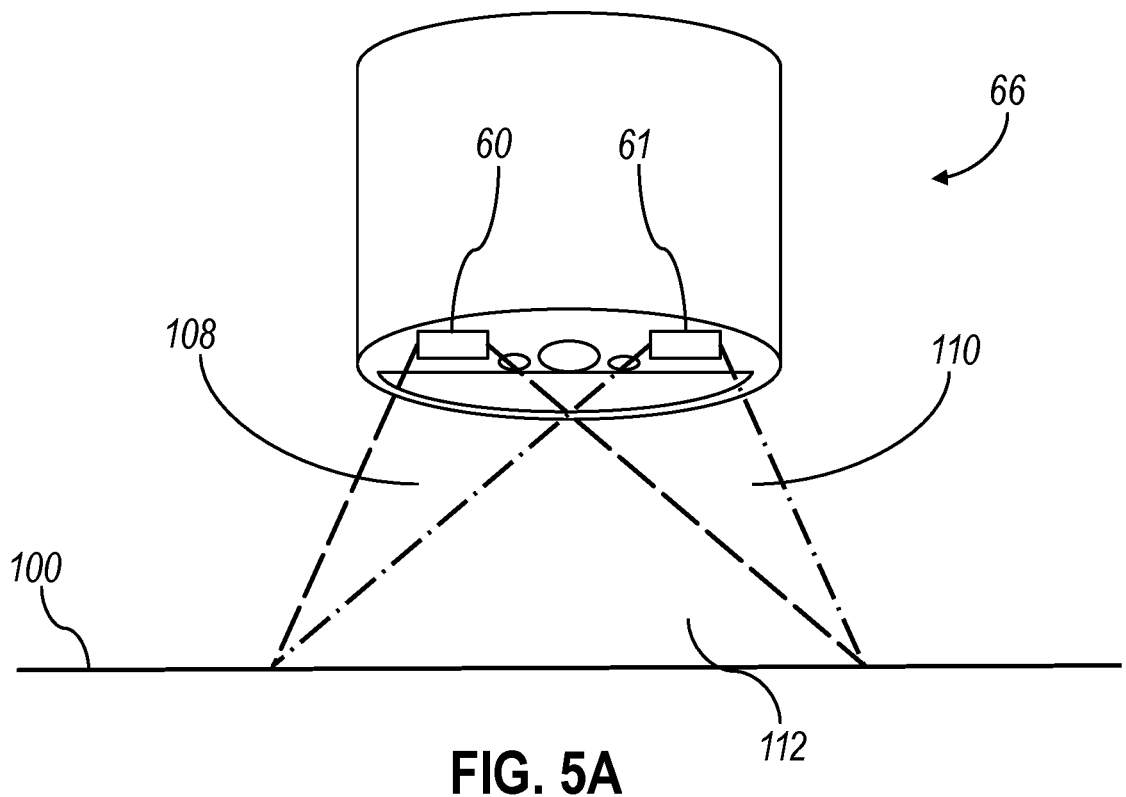
FIG. 5A depicts a side diagrammatic view of an exemplary set of fully overlapping fields of view of the dual camera endoscope of FIG. 2.
Figure 5B:
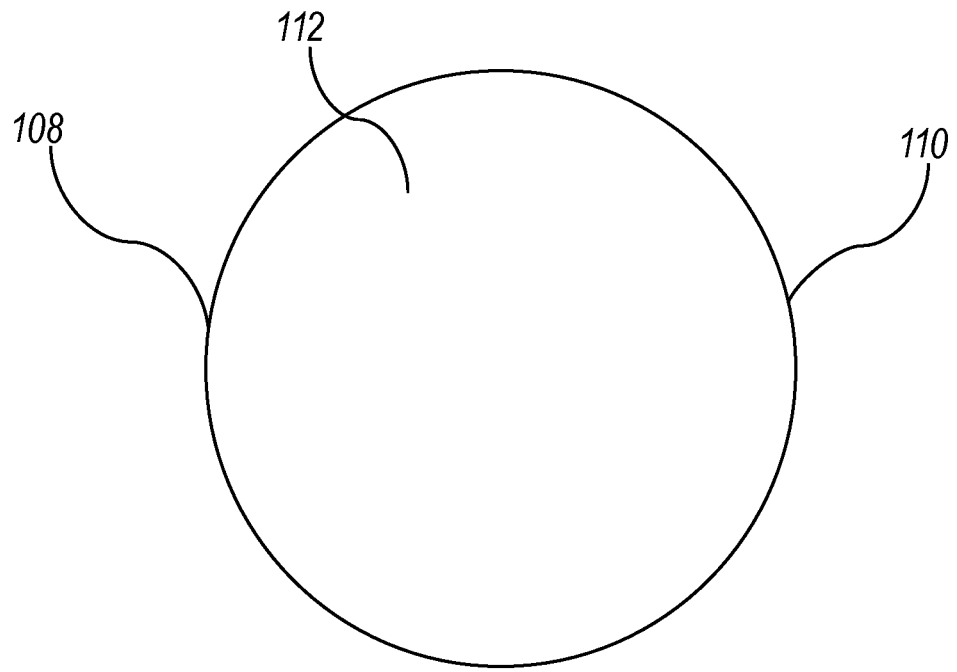
FIG. 5B depicts a top-down diagrammatic view of the set of fully overlapping fields of view of FIG. 5A.

In some implementations, the set of cameras (59) may also be oriented such that their respective lines of sight to the target surface (100) are intersecting, converging, or otherwise oriented toward each other rather than being parallel. For example, FIG. 5A shows a side diagrammatic view of an exemplary set of overlapping fields of view of the dual camera endoscope, while FIG. 5B depicts a top-down diagrammatic view of the set of overlapping fields of view. As can be seen, the first camera (60) and the second camera (61) are oriented such that their respective lines of sight intersect, converge, or are otherwise oriented toward each other. As with the prior example, the first camera (60) provides a first field of view (108)), while the second camera (61) provides a second field of view (110), which combine to provide a combined field of view (112). As can be seen, the first field of view (108) and the second field of view (110) may perfectly or substantially overlap when producing the combined field of view (112). When perfectly overlapping, the unique portions of the first field of view (108) and the second field of view (110) may be non-existent or null values. When substantially overlapping, the unique portions of the first field of view (108) and the second field of view (110) may include negligible portions of image data at each edge of the combined field of view (112).

Comparing FIGS. 4B and 5B, it can be seen that a parallel orientation of the cameras provides a wide overall field of view (e.g., the distance between the outer edges of the first field of view (102) and the second field of view (104) is greater than the distance between the outer edges of the first field of view (108) and the second field of view (110)) and a narrow combined field of view (e.g., the width of the combined field of view (106) is lesser than the width of the combined field of view (112)). An intersecting or converging orientation of the cameras provides a narrower overall field of view, as the first field of view (108) and the second field of view (110) substantially or entirely overlap, but the combined field of view (112) is substantially larger.

Each implementation (e.g., whether maximizing overall width or maximizing width of overlap) may be desirable in some instances. As a brief example, a wide overall field of view such as that of the first field of view (102) and the second field of view (104) may be useful in producing wide shot or panoramic view images. As another example, a wide combined field of view such as that of the combined field of view (112) may be useful in producing upscaled images or images that take advantage of parallax image concepts in order to produce stereoscopic or three-dimensional images. These examples and others will be described in more detail below.

The set of cameras (59) may, in some implementations, be statically oriented with respect to each other in order to provide the most desirable field of view for certain applications. This may include statically orienting the cameras such that their lines of sight are parallel, as shown in FIG. 4A, or statically orienting the cameras such that their lines of sight intersect at various distances (e.g., where an endoscope is typically positioned 2 inches from a surgical site, a static intersecting orientation may be optimized for such a distance).

In other implementations, each camera may be rotatably positioned within the distal tip (66) to allow for a limited amount of side-to-side rotation (e.g., yaw) independently of each other. For example, the first camera (60) may be rotatably installed within a housing such that an electric actuator may extend or retract and change the orientation of the first camera. Alternately, an electroactive polymer may be integrated into a housing that flexibly biases the first camera to rotate in a first direction, such that electric current received via the same connection that the first camera (60) uses for data communications causes the electroactive polymer to shrink and rotate the camera in a second direction. The orientation of the set of cameras may be changed or influenced in varying ways, which will be apparent to one of ordinary skill in the art in light of this disclosure. Such dynamic orientation may be performed manually by use of the control (56) and a pull wire or other mechanical actuator, for example; or may be performed automatically by the processor (12) or another device. As an example, where a focused or converging line of sight of the target surface (100) is desired (e.g., like the configuration shown in FIGS. 5A-5B), the processor (12) may determine the distance between the set of cameras (59) and the target surface (100) and automatically orient each camera (59) in real time so that their lines of sight intersect or converge proximately to the target surface (100), providing an automatically focusing, three-dimensional field of view similar to that of a human. Providing a parallax view in this manner may be advantageous in that it provides a sense of depth perception to a viewer; and provides a level of immersion beyond two-dimensional viewing, which may aid in accurate and precise movements and manipulations of surgical tools and other devices.

III. EXEMPLARY METHODS FOR IMAGE PROCESSING WITH DUAL SENSOR ENDOSCOPE

Figure 6:
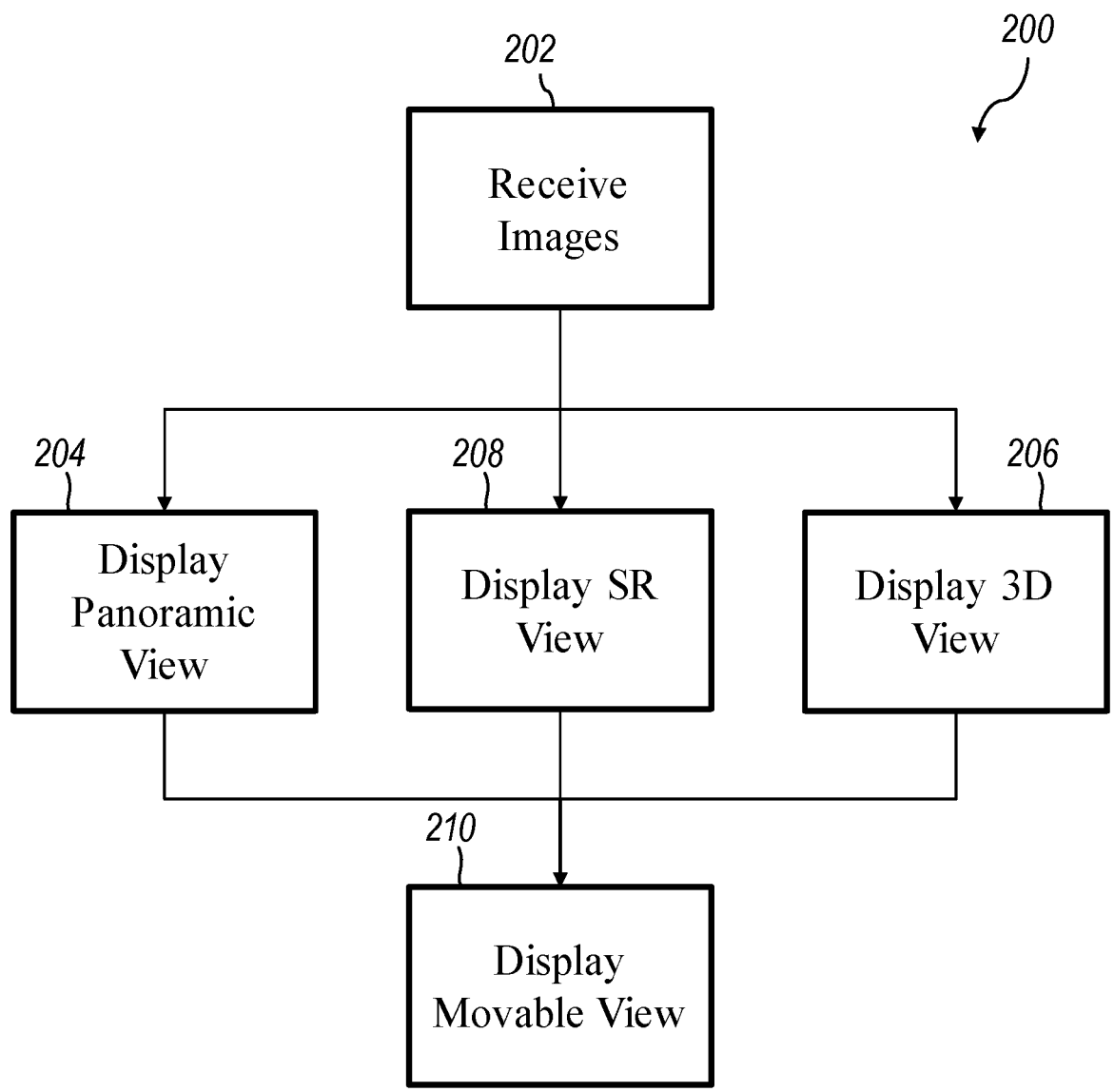
FIG. 6 depicts a flowchart of an exemplary set of steps that may be performed to provide enhanced endoscopic views using the dual camera endoscope of FIG. 2.

An endoscope such as the dual camera endoscope (50) described above may be used to capture additional image data of a surgical site that may be used to create new images and perspectives of a surgical site during a surgical procedure, such as when displayed via the display screen (16). Creating and providing new images of a surgical site provides a surgeon valuable additional information and context throughout a procedure, which may lead to improved patient outcomes. As an example of such features, FIG. 6 depicts a flowchart of an exemplary set of steps (200) that may be performed by a system such as the IGS navigation system (10) to provide enhanced endoscopic views using an endoscope such as the dual camera endoscope (50).

As images are received (block 202) from the set of cameras (59), the system may manipulate the images in one or more ways using the additional image data provided by first camera (60) and the second camera (61) as compared to image data provided by a single camera by itself. This may include creating and displaying (block 204) a panoramic view, creating and displaying (block 208) a super resolution view, or creating and displaying (block 206) a three-dimensional view. A three-dimensional view may include an image viewable with a 3D capable monitor or other device such as a head-mounted display (HMD), such as a side-by-side or over-under set of image data; but may also include an image, an animated image or video image, or other set of images that may be displayed on any type of display and that may give a sense of movement, navigation, or depth even when displayed in two dimensions.

As an example and with reference to FIG. 5B, this may include creating and displaying an animated image that alternates between the first field of view (108) and the second field of view (110), and that may include one or more intervening images produced by gradually morphing or otherwise combining images from the first field of view (108) and the second field of view (110). Such an image may be automatically alternated and displayed in two dimensions, providing a sense of moving and pivoting between the two perspectives (e.g., that of the first camera (60) and that of the second camera (61)). Such an image may also be manually alternated or navigated by a user based upon inputs received via a keyboard, mouse, voice input, or other input type, in order to provide an image that a user may view in two dimensions while moving and pivoting between two perspectives.

Any one or more of these views, as well as views of the original received (block 202) image, may be displayed individually or simultaneously with each other, and may also be displayed (block 210) as a movable view via the display screen (16). A movable view may provide a cropped view of another video or image (e.g., a panoramic view or super resolution view) that may be moved using the operating controls (14) to view different areas of the image at varying levels of detail. For example, a created panoramic view may be too large for the display screen (16) to display at its true size (e.g., a digital image may be 5000×5000 pixels, and a particular display may only support display of 1680×1050 pixels, meaning that larger images are downscaled for display and image details may be lost or obfuscated).

The movable view may be moved about a larger image to show particular sections in increased or full detail (e.g., in the above example, 1680×1050 pixels at a time), and may also be configured to respond to navigational inputs via the operating controls (14) as if it were a moving endoscopic camera (e.g., the image may gradually zoom in or out, move horizontally and vertically, or change an angle or orientation, as an endoscopic being moved within the patient would). In this manner, the movable view may create a sense of movement when repositioning its displayed section, such that a surgeon relying upon the displayed images may perceive that they are actually physically repositioning the source endoscope, which may aid the surgeon in perceiving and understanding the spatial relationship of their view of the surgical site. While FIG. 6 provides a high level description of several exemplary display features, FIGS. 7-10 provide more details on steps that may be performed during one or more of the high level steps.

Figure 7:
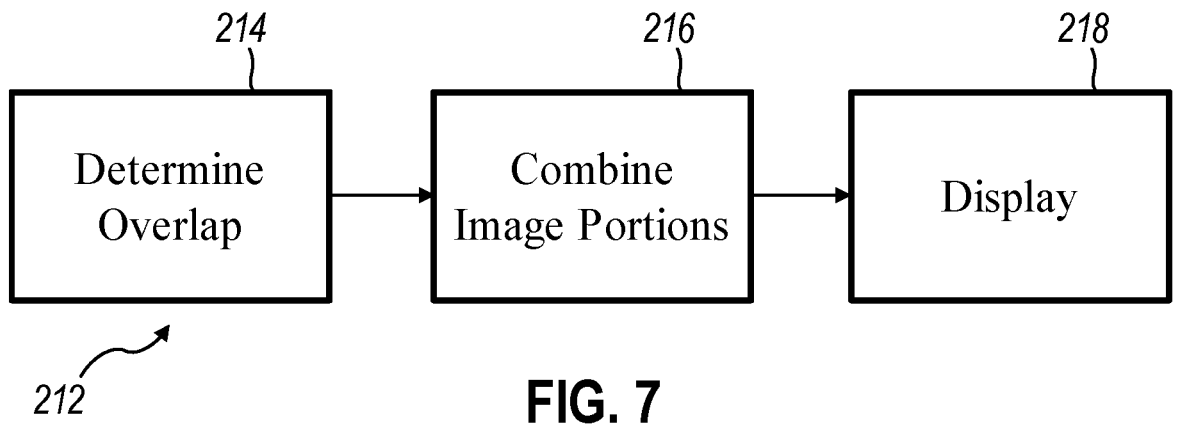
FIG. 7 depicts a flowchart of an exemplary set of steps that may be performed to provide a panoramic endoscopic view using the dual camera endoscope of FIG. 2.

For example, FIG. 7 depicts a flowchart of an exemplary set of steps (212) that may be performed to provide a panoramic endoscopic view using an endoscope such as the dual camera endoscope (50). While it should be understood that the teachings herein may be applied to still image as well as sequences of images (e.g., video), the descriptions and figures may at times refer to singular pairs of images for ease of discussion. When data usable to produce an image is received from the dual camera endoscope (50), the IGS navigation system (10) will have two images, one from the first camera (60) and one from the second camera (61). Where the cameras are statically positioned and oriented for parallel line of sight (e.g., as shown in FIGS. 4A and 4B), the system may determine (block 214) the overlap of the two images based upon known characteristics of the cameras' positions. For example, the combined field of view (106) in FIG. 4B represents an overlap of two images captured by the cameras of that example, and will remain static so long as the cameras do not change their position or orientation, relative to each other. In that implementation, the image overlap may be determined (block 214) and configured prior to the time of capture (e.g., the dual camera endoscope (50) may output image data indicating the overlap as a static value, or the IGS navigation system (10) may be configured with such a value or may access or retrieve such a value based upon the type of endoscope in use).

As another example, where the cameras have a static parallel line of sight as described above, or where the cameras are capable of dynamic intersecting or converging lines of sight (e.g., focusing on an object or target), the amount of overlap may also be determined (block 214) dynamically for an image or video. Such dynamic determination (block 214) may be performed per image (e.g., once for each and every pair of received images during a video sequence of images) or for batches of images at a time (e.g., overlap may be determined (block 214) for a first image, and such overlap may be used for the next thirty images, or for any number of images received during the next second), as desired for a particular implementation and as may be possible for a particular processing device.

Determining overlap dynamically (block 214) may be performed in varying other ways. In some implementations, this could be performed algorithmically using an image processing and comparison algorithm to compare the first image to the second image in order to identify the matching or substantially matching (e.g., where the two cameras are focused on a single point from two slightly different perspectives) portions, or to identify and correlate a recognizable feature or object that is present within each (e.g., a cutting instrument or other surgical tool within the field of view of an endoscope). In some implementations this could be performed using a proximity sensor positioned on the distal tip (66) that could detect the distance between the target surface (100) and the cameras. Such information may be used, along with the relative position and orientation of each camera to the other, to determine the spatial relationship of each image to the other, which will indicate the amount of overlap. In some implementations, this could be performed using a visual marker, such as a laser light, projected by a laser fixed or within each camera and aimed at that camera's point of focus, such that each image would contain that images point of focus at its center, as well as the other images point of focus offset from its center, which could then be used to determine (block 214) overlap. Various other methods for determining (block 214) overlap exist, and will be apparent to one of ordinary skill in the art in light of this disclosure.

Figure 11A:
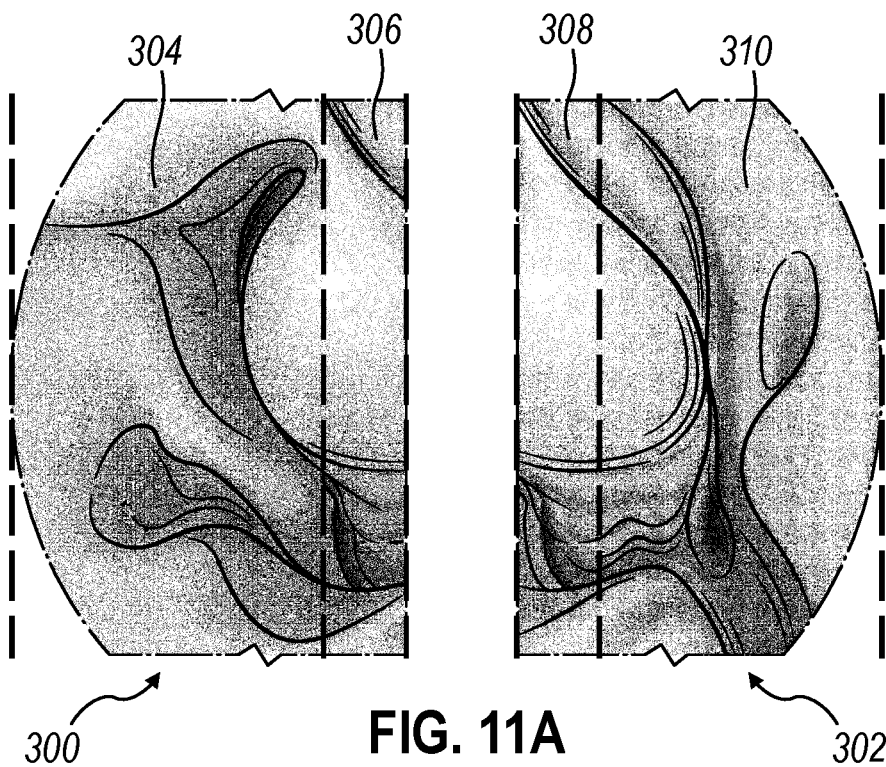
FIG. 11A depicts a diagrammatic view of a set of input images for an exemplary panoramic view.
Figure 11B:
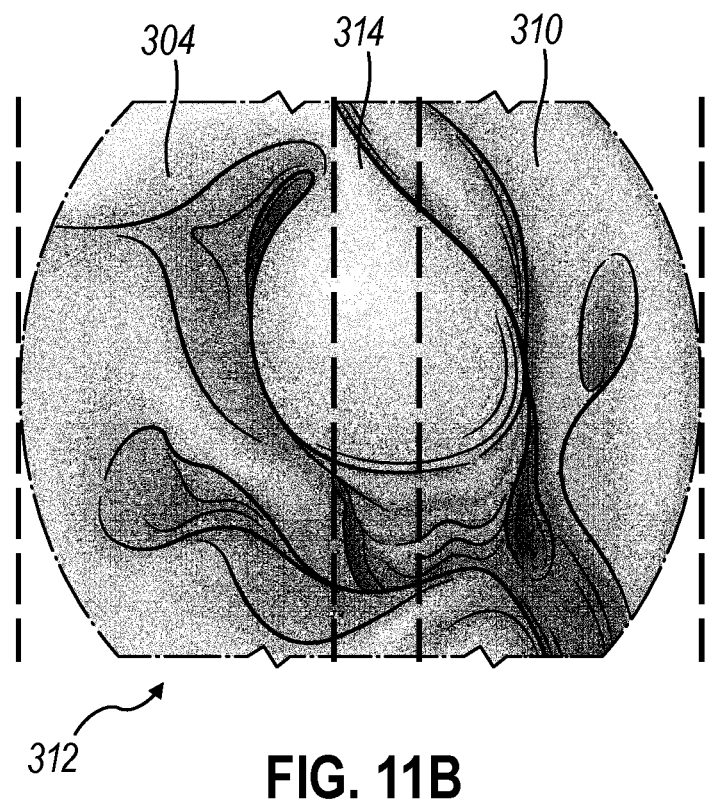
FIG. 11B depicts a diagrammatic view of an output image for the panoramic view of FIG. 11A.

Once overlap has been determined (block 214), the system may then combine (block 216) the two images to create a new panoramic image, and then may display (block 218)

the resulting panoramic image via the display screen (16). As an example, FIG. 11A shows an image (300) such as might be captured by the second camera (61), and an image (302) such as might be captured by the first camera (60). The system may determine (block 214) the overlap of the two images and identify a first outer portion (304), an overlapping portion (306), an overlapping portion (308), and a second outer portion (310) within the images. The system may then combine (block 216) the two images at their unique edges, separated by a single overlapping portion, in order to produce a new panoramic image, such as shown in FIG. 11B. As can be seen in that figure, a new panoramic image (312) has been created by combining the first outer portion (304) with an overlapping portion (314) (e.g., either of the other overlapping portions) and the second outer portion (310). In such an example, supposing that the image (300) and the image (302) each have a horizontal resolution of 2000 pixels, and the overlapping portion (314) has a horizontal resolution of 500 pixels, the panoramic image (312) created as a result would have a total horizontal resolution of about 3500 pixels, providing a significant increase in the area of the image that could be viewable at the highest resolution and detail possible, if desired.

Figure 8:
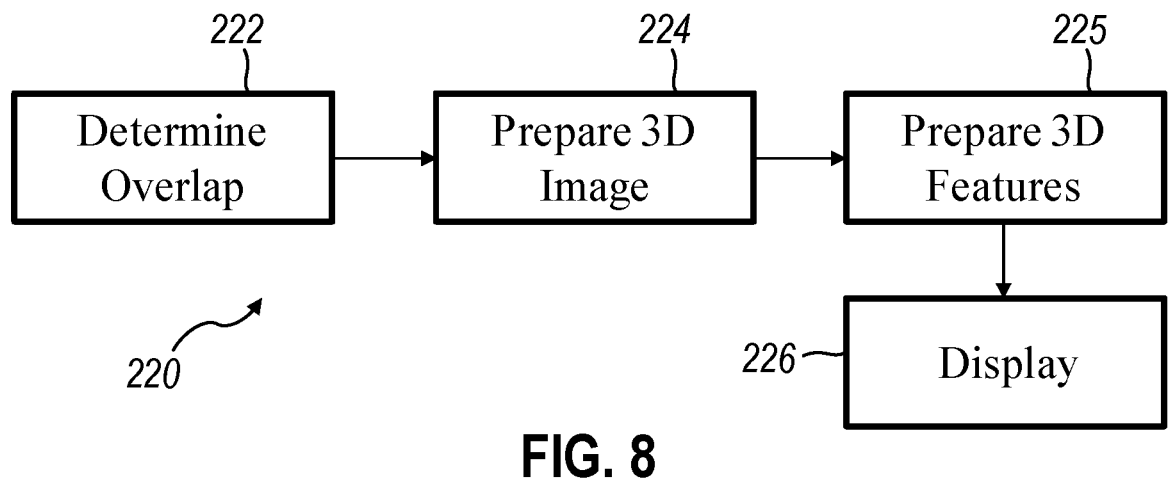
FIG. 8 depicts a flowchart of an exemplary set of steps that may be performed to provide a three-dimensional endoscopic view using the dual camera endoscope of FIG. 2.

FIG. 8 shows a flowchart of an exemplary set of steps (220) that may be performed to provide a three-dimensional endoscopic view using an endoscope such as the dual camera endoscope (50). As with FIG. 7, the system may first determine (block 222) the overlap between the two input images, in order to determine the spatial relationship between the two fields of view from which the images were captured. The system may then prepare (block 224) a 3D image, the format and features of which may be dependent upon a device or devices that it is intended to be viewed on.

For example, in the case of a 3D capable or virtual reality capable HMD, preparing (block 224) a 3D image may include cropping the input images to exclude edge portions or non-overlapping portions, and arranging the remaining image portions side-by-side so that a viewer's eyes can independently focus on the two slightly varying image perspectives when they are displayed (block 226) via the two viewing lenses of the HMD.

As another example, the 3D image may be prepared (block 224) to display on displays capable of displaying 2D images while simulating depth or movement when perspectives, as has been described above. This may include preparing (block 224) the image as an animated image, video image, or one or more side-by-side images, and alternating between displaying images from different perspectives (e.g., one from the first camera (60) and one from the second camera (61)). This may also include producing one or more intervening images by morphing source images from different perspectives to provide multiple viewing angles in between. A 3D image prepared (block 224) to provide one or more of these features may allow a user to view the images in 2D, with the ability to manually or automatically shift perspectives to provide a sense of pivoting or rotating around the target surface (100), as opposed to just panning or moving across it. Viewing such an image may advantageously provide an improved sense of depth and spatial positioning, as opposed to a static 2D image.

Preparing (block 224) the 3D image dataset may also include preparing (block 225) one or more 3D datasets or additional 3D features. For example, some implementations may use 3D image data to produce depth measurements, topographical indicators, or other depth and distance indicators associated with the target surface (100). Such depth indicators may include one or more of a distance marker showing one or more dimensions of an anatomical structure within the 3D field of view. This may be determined by performing a visual analysis and comparison of a targeted anatomical structure from two or more perspectives in order to take advantage of the parallax view and estimate a depth of the targeted object. Another depth indicator may include a topographical map or overlay showing, via variations in displayed colors, patterns, or other visual indicators, topographical characteristics of an anatomical structure within the 3D field of view. This may be also be determined using the captured parallax view; and may be overlaid upon and displayed (block 226) with the source image or displayed (block 226) independently of the source image.

Another example of a 3D feature that may be prepared (blocked 225) using the 3D image data is a measurement of volume of an anatomical structure within the 3D field of view. After determining the depth of an anatomical structure, as described above, the system may also determine a length and width, a circumference, or other dimensional measurements of an anatomical structure. This may include automatically determining the scale of the captured image using information such as the distance between the camera and the anatomical structure (e.g., as provided by a proximity sensor used to focus and converge two fields of view at a target surface or object).

A determination of volume of a targeted anatomical structure may be useful in providing an indication of an amount of tissue, bone, or other material that must be removed or affected during a procedure. A determined volume of an anatomical structure may also be useful to provide a comparison point between pre-operative and post-operative anatomical structures; and may provide an indication of the level of success of a procedure, a patient recovery time, or a need for additional procedures. Such comparisons between pre-operative and post-operative anatomical structures may include visual comparisons of endoscopic images, as well as visual or numeric indicators of change of volume, depth, and topography. A system having one or more of these describes features may also include any of the teachings of U.S. Pat. App. 62/779,614, entitled "Surgical System with Combination of Sensor-Based Navigation and Endoscopy", filed Dec. 14, 2018, the entirety of which is incorporated by reference herein.

Figure 9:
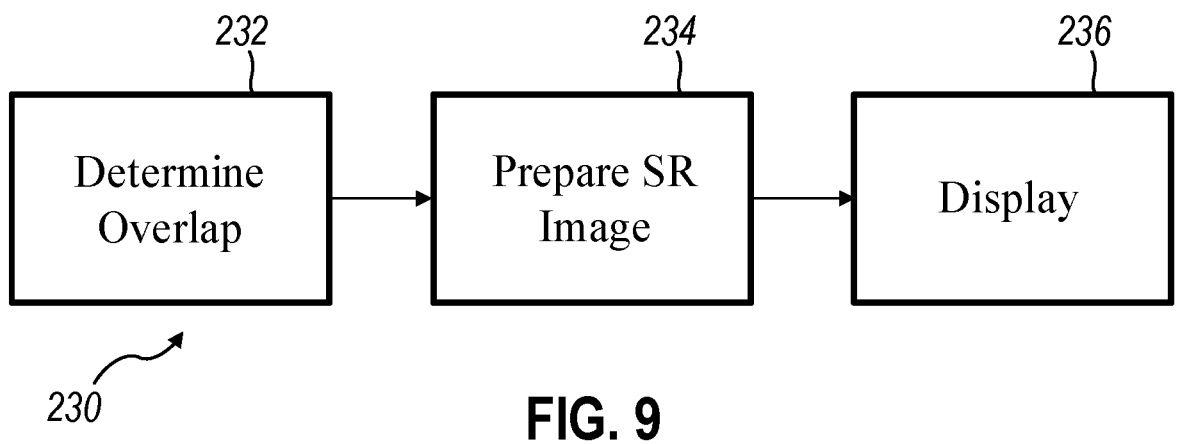
FIG. 9 depicts a flowchart of an exemplary set of steps that may be performed to provide a super resolution endoscopic view using the dual camera endoscope of FIG. 2.

FIG. 9 shows a flowchart of an exemplary set of steps (230) that may be performed to provide a super resolution endoscopic view using an endoscope such as the dual camera endoscope (50). As with prior examples, the system may first determine (block 232) an amount of overlap between the two input images. The system may then prepare (block 234) a super resolution image from the combined, overlapping portions of the two input images, and display (block 236) the resulting image at a higher resolution than its input images. Super resolution is an image processing technique that can combined overlapping or substantially overlapping images in order to produce an output image of higher resolution than its input image data, and with reduced digital noise and other visual artifacts that may be introduced during digital imaging.

Figure 10:
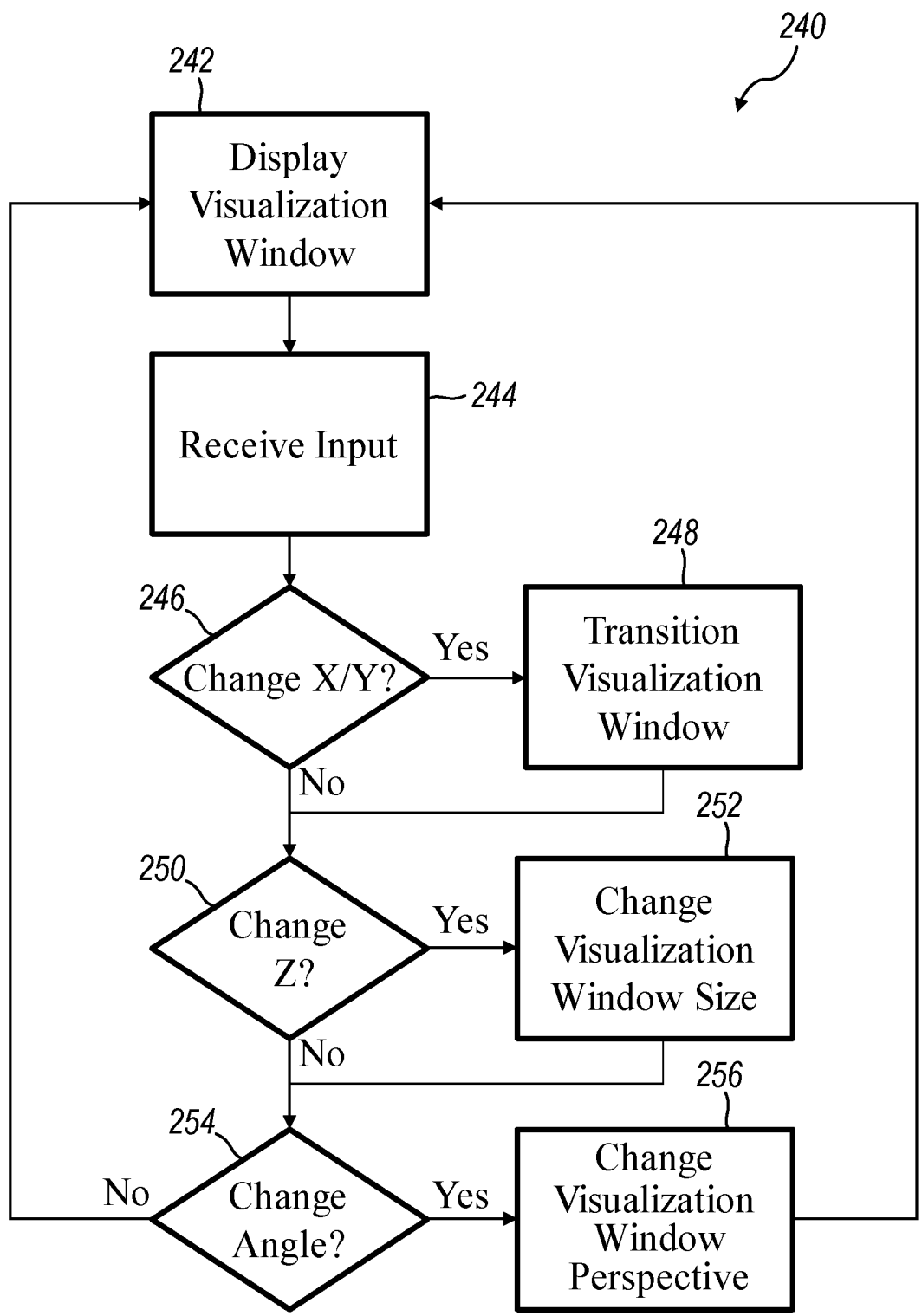
FIG. 10 depicts a flowchart of an exemplary set of steps that may be performed to provide a virtualization window for one or more enhanced endoscopic views.
Figure 12A:
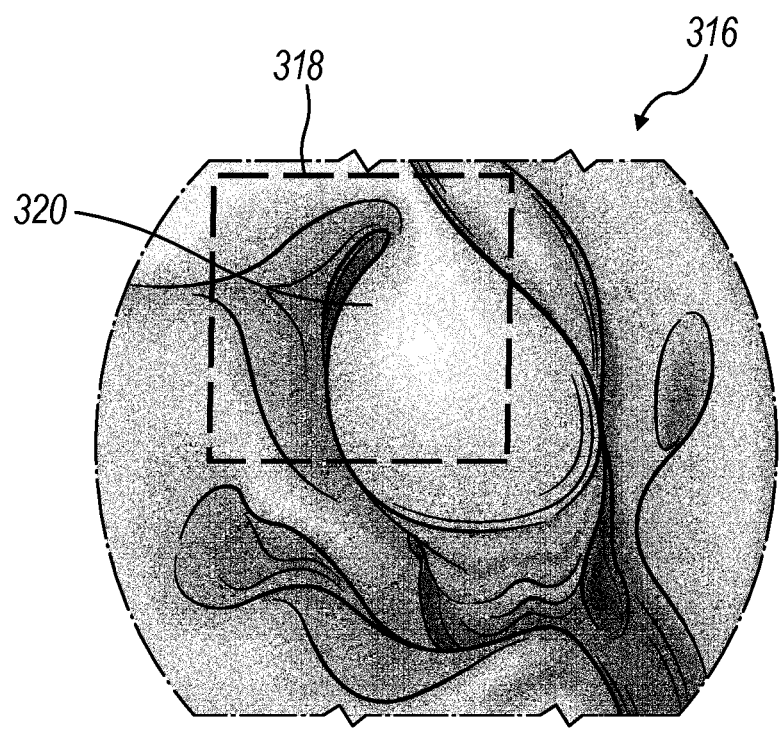
FIG. 12A depicts a diagrammatic view of an input image for an exemplary virtualization window view.
Figure 12B:
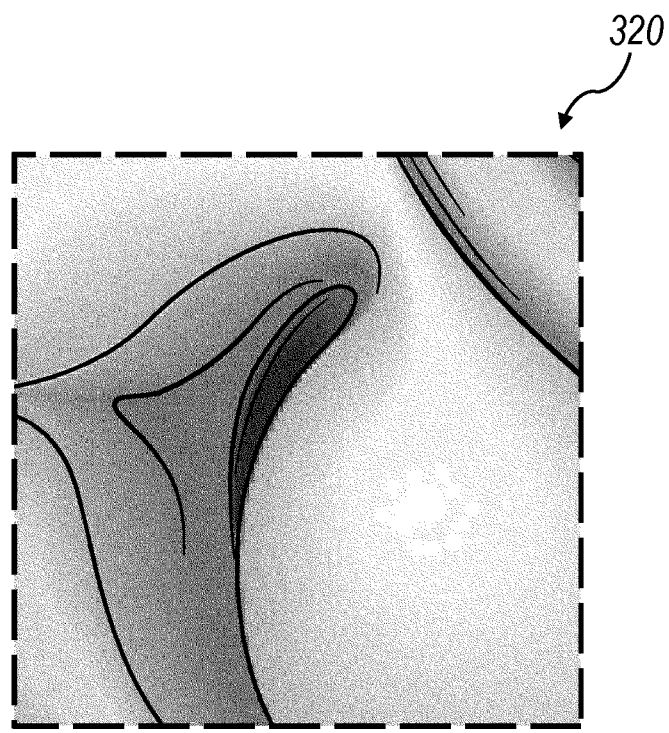
FIG. 12B depicts a diagrammatic view of an output image for the exemplary virtualization window view of FIG. 12A.

Newly created output images, particularly panoramic images and super resolution images may benefit from the display as a movable view, in order to take advantage of their increased resolution while also providing the surgeon or other user a familiar sense of movement and navigation within and around a surgical site, as has been previously discussed. FIG. 10 shows a flowchart of an exemplary set of steps (240) that may be performed to provide movable view, or a visualization window, for one or more enhanced endoscopic views, such as the panoramic view or super resolution view described above. The system may display (block 242) a visualization window via the display screen (16) as a real-time endoscopic image or video, showing a view of a surgical site. The image shown in the visualization window may be a section of a received (block 202) image, or may be a section of an image created from a received (block 202) image by steps such as those shown in FIGS. 7-9. For example, a panoramic image that has been created by combining (block 216) portions of input images may be 3000×2000 while the visualization window may show a 1000×1000 pixel area, meaning that only about 15% of the image may be shown within the visualization window at any one time. As an example, FIG. 12A shows an image (316) captured by an endoscope such as the dual camera endoscope (50), which may be a normal image, panoramic image, super resolution image, or other image type captured or created by the system. A visualization window (318) is depicted as a box overlaid upon the larger image (316). FIG. 12B shows a viewable section (320) of the image (316) that is contained within the visualization window (318). The viewable section (320) may be displayed via the display screen (16) at a desired resolution that is supported by the display screen (16), such that the viewable section (320) the surgical site may be viewed at a high level of detail (e.g., the maximum resolution supported by the display screen (16) without any downscaling) if desired.

A user may interact with a set of user input devices such as the operating controls (14) in order to move and reposition the visualization window (318) on a desired section of the larger image (316). This may include interacting with a touch screen to touch and drag to a new section of an image, interacting with software buttons to move the view in a desired direction, using a keyboard or mouse to scroll the view, and other types of input. As user inputs are received (block 244), the visualization window (318) and resulting display may be updated to reflect a movement of the window relative to the larger image (e.g., the smaller visualization window moving across the larger image to display new sections) or a change in size of the window relative to the larger image (e.g., the size of the section displayed by the visualization window changes, simulating a movement inwards outwards). Changes in the visualization window may be displayed gradually to simulate the feeling or experience of motion within a three dimensional space, such as might be experienced when an endoscope providing the image is actually moved (e.g., moved upwards or downwards, advanced or retracted, orientationally rotated).

Some implementations may also allow the visualization window to be rotated to cause a corresponding change to the orientation of the perspective from which the image is viewed. This may be accomplished by applying image processing algorithms to modify and redisplay the image in real-time. This could produce a visual effect similar to that of the endoscope rotating, or a movable lens of the endoscope rotating (e.g., around the x-axis or the y-axis). Image processing to shift perspectives of an image may benefit from having more detailed and higher resolution input images in order to produce realistic looking, perspective shifted output images, and thus may be advantageously applied to panoramic images, super resolution images, and other images captured or created according to one or more of the techniques described herein.

As inputs are received, the system will determine (block 246) whether they indicate a movement, such as panning, of the visualization window horizontally, vertically, or both, and in response may gradually transition (block 248) the visualization window to the new section. Display in this manner may simulate a movement of the endoscope horizontally (e.g., along the x-axis) and vertically (e.g., along the y-axis) relative to the surgical site or other viewed target.

The system may also determine (block 250) whether the inputs indicate a movement, such as zooming, of the visualization window towards the surgical site or away from the surgical site, and in response may gradually change (block 252) the size or magnification level of the section displayed within the visualization window to the new size. Display in this manner may simulate an advance or withdrawal of the endoscope (e.g., along the z-axis) relative to the surgical site or other viewed target.

The system may also determine (block 254) whether the inputs indicate a rotational change or perspective change of the visualization window relative to surgical site, and in response may gradually change (block 256) the perspective of the section displayed within the visualization window to the new perspective. Change (block 256) of the perspective may be limited within configurable boundaries in order to prevent changes in viewing perspective that would result in perspective shifted output images of low quality (e.g., where automatic reduction or introduction of pixels within an area of the image exceeds a configured threshold) or of a perspective that is so obviously skewed that it breaks the sense of immersion of a viewer.

Display in this manner may simulate a rotational or angular change of the endoscope relative to the surgical site or other viewed target. For example, as discussed above in the context of FIG. 5B, images from the first field of view (108) and the second field of view (110) may be manually panned or pivoted between to provide a sense of pivoting between two perspectives, even when viewed two-dimensionally. Any intervening images that may be produced by gradually morphing between or otherwise combining the two source images from the first camera (60) and the second camera (61) may simulate and be viewable as multiple viewing angles present between the first camera (60) and the second camera (61). The speed and responsiveness of visualization window transitions (block 248), size changes (block 252), and perspectives changes (block 256) may be configured to provide a sense of steady movement within three-dimensional space, while the perspective of the source image and endoscope themselves do not change.

Figure 13A:
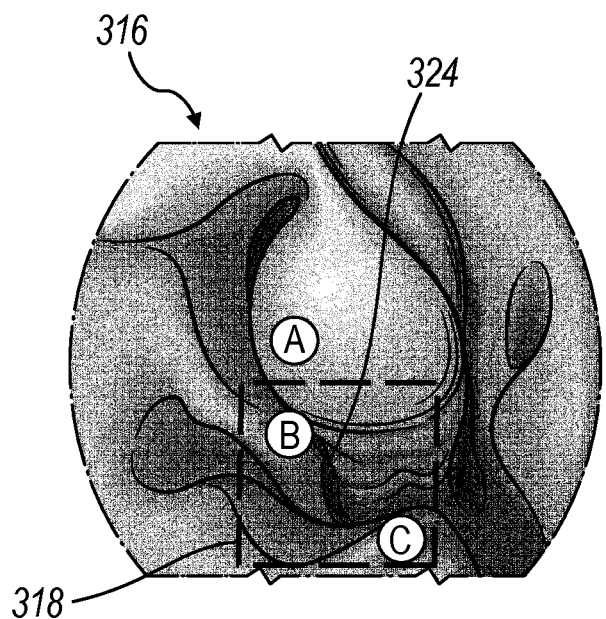
FIG. 13A depicts a diagrammatic view of an input image for the virtualization window view.
Figure 13B:
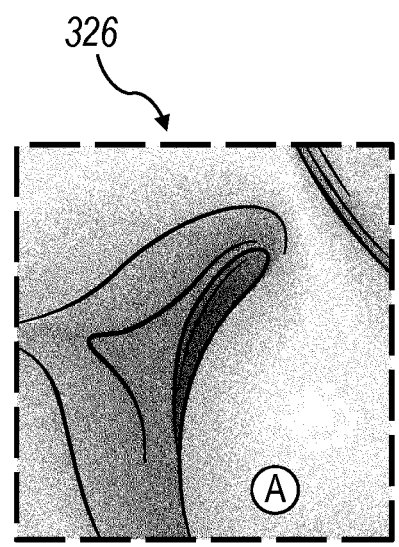
FIG. 13B depicts a diagrammatic view of a first output image during navigation from the view of FIG. 12A to the view of FIG. 13A.
Figure 13C:
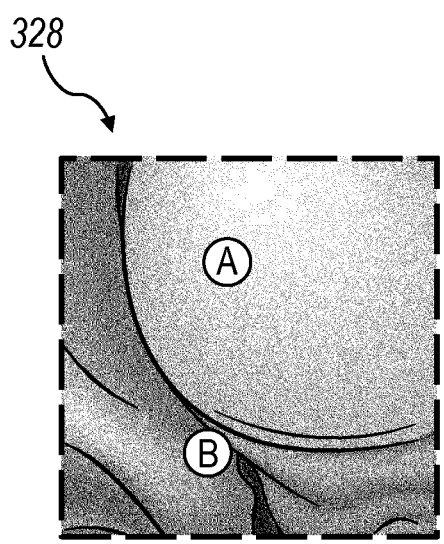
FIG. 13C depicts a diagrammatic view of a second output image during navigation from the view of FIG. 12A to the view of FIG. 13A.
Figure 13D:
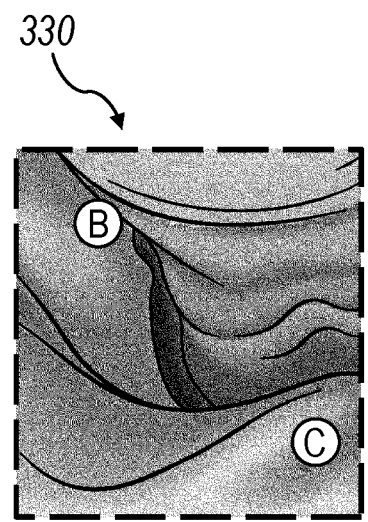
FIG. 13D depicts a diagrammatic view of a third output image during navigation from the view of FIG. 12A to the view of FIG. 13A.

As an example, FIGS. 13A-13D show a set of simulated images that may be displayed during use and navigation of the visualization window, for example, when the visualization window (318) is moved from the position shown in FIG. 12A to the position shown in FIG. 13A. A set of reference points labeled A, B, and C are overlaid upon the source image (316) for the purpose of describing the simulated images. FIG. 13B shows an origin image (326) that displays a section of the source image (316) contained within the visualization window (318) at its starting point shown in FIG. 12A. FIG. 13C shows a transitional image (328) that would be contained within the visualization window (318) as it transitions (block 248) to a new section of the source image (316), as a result of user input. As can be seen by the reference points A and B, the visualization window (318) has moved vertically downwards and horizontally to the right relative to FIG. 13B. FIG. 13D shows a destination image (330) that displays a section of the source image (316) contained within the visualization window (318) at its ending point shown in FIG. 13A. The reference points B and C show that the visualization window (318) has moved vertically downwards and horizontally to the right relative to FIG. 13C. During a transition (block 248) such as described above, any number of transition images as may be desired can be displayed in between the origin and destination to provide a sense of gradual and smooth movement to the destination in response to user input.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system comprising: an endoscope comprising: a coupling unit, a shaft extending from the coupling unit, and a set of cameras positioned at a distal end of the shaft, wherein the set of cameras are operable to capture and communicate image data to the coupling unit; an image processor configured to receive image data from the coupling unit; and a display; wherein the image processor is configured to: receive a first image from a first camera of the set of cameras and receive a second image from a second camera of the set of cameras, determine a first image unique portion, an overlapping portion, and a second image unique portion based on the first image and the second image, create an enhanced image based on the first image unique portion, the overlapping portion, and the second image unique portion, and provide a visualization window that displays a current section of the enhanced image via the display.

Example 2

The system of Example 1, wherein the image processor is further configured to, when creating the enhanced image, combine the first image unique portion, the overlapping portion, and the second image unique portion to create a panoramic image, wherein the panoramic image comprises a higher resolution than the first image and the second image.

Example 3

The system of any one or more of Examples 1 through 2, wherein the image processor is further configured to, when creating the enhanced image: determine that the first image and the second image perfectly or substantially overlap, such that the first image unique portion and the second image unique portion contain no image data or negligible image data, and combine the overlapping portion from the first image and the second image to create a super resolution image, wherein the super resolution image comprises a higher resolution than the overlapping portion.

Example 4

The system of any one or more of Examples 1 through 3, wherein the image processor is further configured to, when creating the enhanced image, create a 3D image of the overlapping portion, wherein the 3D image is configured to be displayed as one or more of: an image that is viewable three-dimensionally on a three-dimensional display, and an image that is viewable three-dimensionally on a two-dimensional display by pivoting back and forth between a first perspective of the overlapping portion and a second perspective of the overlapping portion.

Example 5

The system of any one or more of Examples 1 through 4, wherein the first camera and the second camera are oriented such that the first camera and the second camera have respective lines of sight that are parallel with each other, and wherein the processor is further configured to determine the overlapping portion based on the first image, the second image, and a static overlap value, wherein the static overlap value is determined based upon a distance between the position of the first camera and the second camera on the distal tip.

Example 6

The system of any one or more of Examples 1 through 5, further comprising a set of operating controls, wherein the image processor is further configured to: receive a set of inputs via the set of operating controls, and update the current section displayed in the visualization window based on the set of inputs.

Example 7

The system of Example 6, wherein the image processor is further configured to, where the set of inputs comprises an input indicating a movement of the visualization window along one or more of the x-axis and the y-axis: determine a destination section of the enhanced image based on the input and the current section, and refresh and provide the visualization window using the destination section as the current section.

Example 8

The system of Example 7, wherein the image processor is further configured to, when refreshing and providing the visualization window using the destination section as the current section: determine one or more transition sections of the enhanced image located between the current section and the destination section, and display the one or more transition sections in an ordered sequence prior to displaying the destination section.

Example 9

The system of any one or more of Examples 6 through 8, wherein the image processor is further configured to, where the set of inputs comprises an input indicating a movement of the visualization window along the z-axis: determine a new magnification level based on the input, and refresh and redisplay the visualization window based on the current section and the new magnification level.

Example 10

The system of Example 9, wherein the image processor is further configured to, when refreshing and providing the visualization window based on the current section and the new magnification level: determine one or more transition magnifications of the enhanced image located between the current section at an original magnification level and the current section at the new magnification level, and display the one or more transition magnifications in an ordered sequence prior to displaying the current section at the new magnification level.

Example 11

The system of any one or more of Examples 6 through 10, wherein the image processor is further configured to, where the set of inputs comprises an input indicating a rotation of a perspective of the visualization window: determine a destination perspective based on the input, digitally alter the current section of the enhanced image based on the destination perspective, and refresh and provide the visualization window based on the digitally altered current section.

Example 12

The system of Example 11, wherein the processor is further configured to, when creating the enhanced image, combine the first image and the second image to produce a third image, wherein the third image comprises a higher resolution than the first image and the second image.

Example 13

The system of any one or more of Examples 1 through 12, wherein each camera of the set of cameras comprises a digital imaging device, wherein each camera of the set of cameras is configured to provide image data to the coupling unit via a conductive connection within the shaft, and wherein the image processor is a processor of an image guided surgery navigation system.

Example 14

A method comprising: positioning an endoscope at a surgical site, wherein the endoscope comprises a first camera and a second camera positioned at a distal end of a shaft of the endoscope; at an image processor, receiving a first image from the first camera and a second image from the second camera, wherein the first and second images are captured simultaneously; determining a first image unique portion, an overlapping portion, and a second image unique portion based on the first image and the second image; creating an enhanced image based on the first image unique portion, the overlapping portion, and the second image unique portion; and providing a visualization window that displays a current section of the enhanced image via a display.

Example 15

The method of Example 14, further comprising, when creating the enhanced image, combining the first image unique portion, the overlapping portion, and the second image unique portion to create a panoramic image, wherein the panoramic image comprises a higher resolution than the first image and the second image.

Example 16

The method of any one or more of Examples 14 through 15, further comprising, when creating the enhanced image: determining that the first image and the second image perfectly or substantially overlap, such that the first image unique portion and the second image unique portion contain no image data or negligible image data; and combining the overlapping portion from the first image and the second image to create a super resolution image, wherein the super resolution image comprises a higher resolution than the overlapping portion.

Example 17

The method of any one or more of Examples 14 through 16, further comprising: receiving a set of inputs via a set of operating controls; where an input of the set of inputs indicates a movement of the visualization window along one or more of the x-axis and the y-axis, determining a destination section of the enhanced image based on the input and the current section; determining one or more transition sections of the enhanced image located between the current section and the destination section; and displaying the one or more transition sections in an ordered sequence prior to displaying the destination section.

Example 18

The method of any one or more of Examples 14 through 17, further comprising: receiving a set of inputs via a set of operating controls; where an input of the set of inputs indicates a movement of the visualization window along the z-axis, determining a new magnification level based on the input; determining one or more transition magnifications of the enhanced image located between the current section at an original magnification level and the current section at the new magnification level; and displaying the one or more transition magnifications in an ordered sequence prior to displaying the current section at the new magnification level.

Example 19

The method of any one or more of Examples 14 through 18, further comprising: receiving a set of inputs via a set of operating controls; where an input of the set of inputs indicates a rotation of a perspective of the visualization window, determining a destination perspective based on the input; determining one or more transitional perspectives of the enhanced image located between a current perspective and the destination perspective; and digitally altering the current section to display the current section at each of the one or more transitional perspectives prior to displaying the current section at the destination perspective.

Example 20

An endoscope comprising: a coupling unit operable to communicate with an image processor; a flexible shaft extending from the coupling unit, the flexible shaft comprising a distal end; a set of cameras positioned on the distal end, wherein each of the set of cameras are operable to capture and communicate image data to the coupling unit via a conductive connection in the flexible shaft; a set of irrigation channels within the flexible shaft, wherein each irrigation channel of the set of irrigation channels transports a received liquid from a proximal end of the flexible shaft to a cover of a camera of the set of cameras at the distal tip; and an instrument channel within the flexible shaft, wherein the instrument channel guides a flexible surgical instrument from the proximal end of the flexible shaft to the distal tip.

V. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system comprising:
    (a) an endoscope comprising:
        (i) a coupling unit,
        (ii) a shaft extending from the coupling unit, and
        (iii) a set of cameras positioned at a distal end of the shaft, wherein the set of cameras are operable to capture and communicate image data to the coupling unit;
    (b) an image processor configured to receive image data from the coupling unit; and
    (c) a display;
    wherein the image processor is configured to:
        (i) receive a first image from a first camera of the set of cameras and receive a second image from a second camera of the set of cameras,
        (ii) determine a first image unique portion, an overlapping portion, and a second image unique portion based on the first image and the second image, wherein the first image unique portion and the second image unique portion are each defined as not overlapping with another image portion,
        (iii) create an enhanced image based on the first image unique portion, the overlapping portion, and the second image unique portion, and
        (iv) provide a visualization window that displays a partial section of the enhanced image via the display, wherein the partial section shows a greater level of image detail than portions of the enhanced image not forming a part of the partial section.

2. The system of claim 1, wherein the image processor is further configured to, when creating the enhanced image, combine the first image unique portion, the overlapping portion, and the second image unique portion to create a panoramic image, wherein the panoramic image comprises a higher resolution than the first image and the second image.

3. The system of claim 1, wherein the image processor is further configured to, when creating the enhanced image:
    (i) determine that the first image and the second image perfectly or substantially overlap, such that the first image unique portion and the second image unique portion contain no image data or negligible image data, and (ii) combine the overlapping portion from the first image and the second image to create a super resolution image, wherein the super resolution image comprises a higher resolution than the overlapping portion.

4. The system of claim 1, wherein the image processor is further configured to, when creating the enhanced image, create a 3D image of the overlapping portion, wherein the 3D image is configured to be displayed as one or more of:
 (i) an image that is viewable three-dimensionally on a three-dimensional display, and
 (ii) an image that is viewable three-dimensionally on a two-dimensional display by pivoting back and forth between a first perspective of the overlapping portion and a second perspective of the overlapping portion.

5. The system of claim 1, wherein the first camera and the second camera are oriented such that the first camera and the second camera have respective lines of sight that are parallel with each other, and wherein the processor is further configured to determine the overlapping portion based on the first image, the second image, and a static overlap value, wherein the static overlap value is determined based upon a distance between the position of the first camera and the second camera on the distal tip.

6. The system of claim 1, further comprising a set of operating controls, wherein the image processor is further configured to:
 (i) receive a set of inputs via the set of operating controls, and
 (ii) update the partial section displayed in the visualization window based on the set of inputs.

7. The system of claim 6, wherein the image processor is further configured to, where the set of inputs comprises an input indicating a movement of the visualization window along one or more of the x-axis and the y-axis:
 (i) determine a destination section of the enhanced image based on the input and the partial section, and
 (ii) refresh and provide the visualization window using the destination section as the partial section.

8. The system of claim 7, wherein the image processor is further configured to, when refreshing and providing the visualization window using the destination section as the partial section:
 (i) determine one or more transition sections of the enhanced image located between the partial section and the destination section, and
 (ii) display the one or more transition sections in an ordered sequence prior to displaying the destination section.

9. The system of claim 6, wherein the image processor is further configured to, where the set of inputs comprises an input indicating a movement of the visualization window along the z-axis:
 (i) determine a new magnification level based on the input, and
 (ii) refresh and redisplay the visualization window based on the partial section and the new magnification level.

10. The system of claim 9, wherein the image processor is further configured to, when refreshing and providing the visualization window based on the partial section and the new magnification level:
 (i) determine one or more transition magnifications of the enhanced image located between the partial section at an original magnification level and the partial section at the new magnification level, and
 (ii) display the one or more transition magnifications in an ordered sequence prior to displaying the partial section at the new magnification level.

11. The system of claim 6, wherein the image processor is further configured to, where the set of inputs comprises an input indicating a rotation of a perspective of the visualization window:
 (i) determine a destination perspective based on the input,
 (ii) digitally alter the partial section of the enhanced image based on the destination perspective, and
 (iii) refresh and provide the visualization window based on the digitally altered partial section.

12. The system of claim 11, wherein the processor is further configured to, when creating the enhanced image, combine the first image and the second image to produce a third image, wherein the third image comprises a higher resolution than the first image and the second image.

13. The system of claim 1, wherein each camera of the set of cameras comprises a digital imaging device, wherein each camera of the set of cameras is configured to provide image data to the coupling unit via a conductive connection within the shaft, and wherein the image processor is a processor of an image guided surgery navigation system.

14. A method comprising:
 (a) positioning an endoscope at a surgical site, wherein the endoscope comprises a first camera and a second camera positioned at a distal end of a shaft of the endoscope;
 (b) at an image processor, receiving a first image from the first camera and a second image from the second camera, wherein the first and second images are captured simultaneously;
 (c) determining a first image unique portion, an overlapping portion, and a second image unique portion based on the first image and the second image, wherein the first image unique portion and the second image unique portion are each defined as not overlapping with another image portion;
 (d) creating an enhanced image based on the first image unique portion, the overlapping portion, and the second image unique portion;
 (e) providing a visualization window that displays a partial section of the enhanced image via a display; and
 (f) receiving a set of inputs via a set of operating controls, wherein an input of the set of inputs indicates a movement of the visualization window.

15. The method of claim 14, further comprising, when creating the enhanced image, combining the first image unique portion, the overlapping portion, and the second image unique portion to create a panoramic image, wherein the panoramic image comprises a higher resolution than the first image and the second image.

16. The method of claim 14, further comprising, when creating the enhanced image:
 (a) determining that the first image and the second image perfectly or substantially overlap, such that the first image unique portion and the second image unique portion contain no image data or negligible image data; and
 (b) combining the overlapping portion from the first image and the second image to create a super resolution image, wherein the super resolution image comprises a higher resolution than the overlapping portion.

17. The method of claim 14, upon receiving the set of inputs via the set of operating controls, further comprising:
 (a) where an input of the set of inputs indicates a movement of the visualization window along one or more of the x-axis and the y-axis, determining a destination section of the enhanced image based on the input and the partial section;

(b) determining one or more transition sections of the enhanced image located between the partial section and the destination section; and (c) displaying the one or more transition sections in an ordered sequence prior to displaying the destination section.

18. The method of claim 14, upon receiving the set of inputs via the set of operating controls, further comprising:

(a) where an input of the set of inputs indicates a movement of the visualization window along the z-axis, determining a new magnification level based on the input;

(b) determining one or more transition magnifications of the enhanced image located between the partial section at an original magnification level and the partial section at the new magnification level; and (c) displaying the one or more transition magnifications in an ordered sequence prior to displaying the partial section at the new magnification level.

19. The method of claim 14, upon receiving the set of inputs via the set of operating controls, further comprising:

(a) where an input of the set of inputs indicates a rotation of a perspective of the visualization window, determining a destination perspective based on the input;

(b) determining one or more transitional perspectives of the enhanced image located between a current perspective and the destination perspective; and (c) digitally altering the partial section to display the partial section at each of the one or more transitional perspectives prior to displaying the partial section at the destination perspective.

20. An endoscope comprising:

(a) a coupling unit operable to communicate with an image processor;

(b) a flexible shaft extending from the coupling unit, the flexible shaft comprising a distal end;

(c) a set of cameras positioned on the distal end, wherein each of the set of cameras are operable to capture and communicate image data to the coupling unit via a conductive connection in the flexible shaft;

(d) a set of irrigation channels within the flexible shaft, wherein each irrigation channel of the set of irrigation channels transports a received liquid from a proximal end of the flexible shaft to a cover of a camera of the set of cameras at the distal tip; and (e) an instrument channel within the flexible shaft, wherein the instrument channel guides a flexible surgical instrument from the proximal end of the flexible shaft to the distal tip.

* * * * *